United States Patent [19]
Ciliberto et al.

[11] Patent Number: 5,972,902
[45] Date of Patent: Oct. 26, 1999

[54] DNA ENCODING HUMAN IL-6 RECEPTOR ANTAGONIST AND PROTEIN ENCODED THEREBY

[76] Inventors: Gennaro Ciliberto, V.le Gorgia di Leontini 330/19 I-00124 Casalpalocco, Rome, Italy; Rocco Savino, Via della Tecnica 76 I-00040, Rome, Italy; Giacomo Paonessa, Via Sofocle 65 I-00125, Rome, Italy

[21] Appl. No.: 08/945,529

[22] PCT Filed: Apr. 26, 1996

[86] PCT No.: PCT/IT96/00084

§ 371 Date: Oct. 28, 1997

§ 102(e) Date: Oct. 28, 1997

[87] PCT Pub. No.: WO96/34104

PCT Pub. Date: Oct. 31, 1996

[30] Foreign Application Priority Data

Apr. 28, 1995 [IT] Italy ................................ RM95A0273

[51] Int. Cl.$^6$ ............................. C07K 14/54; C12N 5/10; C12N 15/24; A61K 38/20
[52] U.S. Cl. .................... 514/44; 424/85.2; 435/69.52; 435/252.3; 435/325; 435/320.1; 435/71.2; 435/471; 536/23.5; 530/351
[58] Field of Search .................... 424/85.1, 85.2; 530/351; 930/140, 141; 514/2, 12, 44; 536/23.1, 23.5; 435/7.1, 69.52, 7.21, 252.3, 325, 320.1, 471, 71.1, 71.2

[56] References Cited

FOREIGN PATENT DOCUMENTS

WO94/09138 4/1994 WIPO.
WO95/00852 1/1995 WIPO.

OTHER PUBLICATIONS

EMBO Journal, vol. 13, No. 24, 1996, Eynsham, Oxford, GB, pp. 5863–5870, XP002012981. Savino, R. et al., Rational design of a receptor super–antagonists of human Interleukin–6.

EMBO Journal, vol. 14, No. 9, 1995, Eynsham, Oxford, GB, pp. 1942–1951, XP000565718. Paonessa, G. et al., "Two distinct and independent sites on iL–6 trigger gp130 dimer formation and signalling".

Proc. of the Amer. Assoc. for Cancer Res. Annual Meeting, vol. 37, No. 0, 1996, pp. 410–411, XP000601653. Borsellino, N. et al., "Effects of an iL–6 receptor super–antagonist (iL–6R Sant 7) on the growth and sensitivity to etoposide (VP–16) of the hormone–Resistant and iL–6–secreting prostate tumor PC–3 cell line."

*Primary Examiner*—Prema Mertz

[57] ABSTRACT

The present invention relates to human interleukin-6 receptor antagonists which are incapable of binding to the receptor chain responsible for transduction of the signal associated with interleukin-6, namely, gp130. The present invention also relates to DNA encoding human interleukin-6 receptor antagonists.

17 Claims, 3 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 555 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
CCAGTACCCC CAGGAGAAGA TTCCAAAGAT GTAGCCGCCC CACACAGACA GCCACTCACG      60

AGCTCAGAAC GAATTGACAA ACAAATTCGG GACATCCTCG ACTTTATCTC AGCCTTAAGA     120

AAGGAGACAT GTAACAAGAG TAACATGTGT GAAAGCAGCA AAGAGGCACT GGCAGAAAAC     180

AACCTGAACC TTCCAAAGAT GGCTGAAAAA GATGGATGCT TCCAATCTGG ATTCAATGAG     240

GAGACTTGCC TGGTGAAAAT CATCACTGGT CTTCTCGAGT TTGAGGTATA CCTAGAGTAC     300

CTCCAGAACA GATTTGAGAG TAGTGAGGAA CAAGCCAGAG CTGTCCAGAT GCGCACAAAA     360

GACCTGATCC AGTTCCTGCA GAAAAAGGCA AAGAATCTAG ATGCAATAAC CACCCCTGAC     420

CCAACCACAA ATGCCAGCCT GCTGACGAAG CTTCAGGCAC AGAACCAGTG GCTGCAGGAC     480

ATAACAACTC ATCTCATTCT GCGCAGCTTT AAGGAGTTCC TGCAGTCCAG CCTGAGGGCT     540

CTTCGGCAAA TGTAG                                                     555
```

(2) INFORMATION FOR SEQ ID NO:2:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
CGCTGACGAA GCTTCAGGCA CAGAACCAGY GGCTGCAGCG TATGACAACT GATCTCATTC      60
```

(2) INFORMATION FOR SEQ ID NO:3:

(i) SEQUENCE CHARACTERISTICS:

(A) LENGTH: 64 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
GCTGACGAAG CTTCAGGCAC AGAACCAGTG GCTGCAGGAC ATGGACACTC ATCTCATTCT      60

GCGC                                                                    64
```

(2) INFORMATION FOR SEQ ID NO:4:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
CCAGTACCCC CAGGAGAAGA TTCCAAAGAT GTAGCCGCCC CACACAGACA GCCACTCACG      60

AGCTCAGAAC GAATTGACAA ACAAATTCGG GACATCCTCG ACTTTATCTC AGCCTTAAGA     120

AAGGAGACAT GTAACAAGAG TAACATGTGT GAAAGCAGCA AAGAGGCACT GGCAGAAAAC     180

AACCTGAACC TTCCAAAGAT GGCTGAAAAA GATGGATGCT TCCAATCTGG ATTCAATGAG     240

GAGACTTGCC TGGTGAAAAT CATCACTGGT CTTCTCGAGT TTGAGGTATA CCTAGAGTAC     300

CTCCAGAACA GATTTGAGAG TAGTGAGGAA CAAGCCAGAG CTGTCCAGAT GCGCACAAAA     360

GACCTGATCC AGTTCCTGCA GAAAAAGGCA AAGAATCTAG ATGCAATAAC CACCCCTGAC     420

CCAACCACAA ATGCCAGCCT GCTGACGAAG CTTCAGGCAC AGAACCAGTG GCTGCAGGAC     480

ATAACAACTC ATCTCATTCT GCGCAGCTTT AAGGAGTTCC TGCAGTCCAG CCTGAGGGCT     540

CTTCGGCAAA TGTAG                                                      555
```

(2) INFORMATION FOR SEQ ID NO:5:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
CCAGTACCCC CAGGAGAAGA TTCCAAAGAT GTAGCCGCCC CACACAGACA GCCACTCACG      60

AGCTCAGAAC GAATTGACAA ACAAATTCGG GACATCCTCG ACTTTATCTC AGCCTTAAGA     120

AAGGAGACAT GTAACAAGAG TAACATGTGT GAAAGCAGCA AAGAGGCACT GGCAGAAAAC     180

AACCTGAACC TTCCAAAGAT GGCTGAAAAA GATGGATGCT TCCAATCTGG ATTCAATGAG     240

GAGACTTGCC TGGTGAAAAT CATCACTGGT CTTCTCGAGT TTGAGGTATA CCTAGAGTAC     300

CTCCAGAACA GATTTGAGAG TAGTGAGGAA CAAGCCAGAG CTGTCCAGAT GCGCACAAAA     360

GACCTGATCC AGTTCCTGCA GAAAAAGGCA AAGAATCTAG ATGCAATAAC CACCCCTGAC     420

CCAACCACAA ATGCCAGCCT GCTGACGAAG CTTCAGGCAC AGAACCAGTG GCTGCAGGAC     480

ATAACAACTC ATCTCATTCT GCGCAGCTTT AAGGAGTTCC TGCAGTCCAG CCTGAGGGCT     540

CTTCGGCAAA TGTAG                                                      555
```

(2) INFORMATION FOR SEQ ID NO:6:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

```
CCAGTACCCC CAGGAGAAGA TTCCAAAGAT GTAGCCGCCC CACACAGACA GCCACTCACG    60
AGCTCAGAAC GAATTGACAA ACAAATTCGG GACATCCTCG ACTTTATCTC AGCCTTAAGA   120
AAGGAGACAT GTAACAAGAG TAACATGTGT GAAAGCAGCA AGAGGCACT GGCAGAAAAC    180
AACCTGAACC TTCCAAAGAT GGCTGAAAAA GATGGATGCT TCCAATCTGG ATTCAATGAG   240
GAGACTTGCC TGGTGAAAAT CATCACTGGT CTTCTCGAGT TTGAGGTATA CCTAGAGTAC   300
CTCCAGAACA GATTTGAGAG TAGTGAGGAA CAAGCCAGAG CTGTCCAGAT GCGCACAAAA   360
GACCTGATCC AGTTCCTGCA GAAAAAGGCA AAGAATCTAG ATGCAATAAC CACCCCTGAC   420
CCAACCACAA ATGCCAGCCT GCTGACGAAG CTTCAGGCAC AGAACCAGTG GCTGCAGGAC   480
ATAACAACTC ATCTCATTCT GCGCAGCTTT AAGGAGTTCC TGCAGTCCAG CCTGAGGGCT   540
CTTCGGCAAA TGTAG                                                   555
```

(2) INFORMATION FOR SEQ ID NO:7:

(i) SEQUENCE CHARACTERISTICS:
        (A) LENGTH: 555 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
CCAGTACCCC CAGGAGAAGA TTCCAAAGAT GTAGCCGCCC CACACAGACA GCCACTCACG    60
AGCTCAGAAC GAATTGACAA ACAAATTCGG GACATCCTCG ACTTTATCTC AGCCTTAAGA   120
AAGGAGACAT GTAACAAGAG TAACATGTGT GAAAGCAGCA AGAGGCCGA CGCATTCTGG    180
AACCTGAACC TTCCAAAGAT GGCTGAAAAA GACGGATGCT TCTACAAAGG ATTCAATGAG   240
GAGACTTGCC TGGTGAAAAT CATCACTGGT CTTTTCGAGT TTGAGGTATA CCTAGAGTAC   300
CTCCAGAACA GATTTGAGAG TAGTGAGGAA CAAGCCAGAG CTGTCCAGAT GCGCACAAAA   360
GACCTGATCC AGTTCCTGCA GAAAAAGGCA AAGAATCTAG ATGCAATAAC CACCCCTGAC   420
CCAACCACAA ATGCCAGCCT GCTGACGAAG CTGCAGGCAC AGAACCAGTG GCTGCAGGAC   480
ATGACAACTC ATCTCATTCT GCGCAGCTTT AAGGAGTTCC TGAUCCGTAG CCTGAGGGCT   540
CTTCGGGCTA TGTAG                                                   555
```

(2) INFORMATION FOR SEQ ID NO:8:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Pro Val Pro Pro Gly Glu Asp Ser Lys Asp Val Ala Ala Pro His Arg
 1               5                  10                  15
```

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Leu Ala Glu Asn Asn Leu Asn Leu
 50                  55                  60

Pro Lys Met Ala Glu Lys Asp Gly Cys Phe Gln Ser Gly Phe Asn Glu
 65                  70                  75                  80

Glu Thr Cys Leu Val Lys Ile Ile Thr Gly Leu Leu Glu Phe Glu Val
                 85                  90                  95

Tyr Leu Glu Tyr Leu Gln Asn Arg Phe Glu Ser Ser Glu Glu Gln Ala
                100                 105                 110

Arg Ala Val Gln Met Arg Thr Lys Asp Leu Ile Gln Phe Leu Gln Lys
                115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Asp
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
                180

(2) INFORMATION FOR SEQ ID NO:9:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Pro Val Pro Pro Gly Glu Asp Ser Lys Asp Val Ala Ala Pro His Arg
 1               5                  10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Leu Ala Glu Asn Asn Leu Asn Leu
 50                  55                  60

Pro Lys Met Ala Glu Lys Asp Gly Cys Phe Gln Ser Gly Phe Asn Glu
 65                  70                  75                  80

Glu Thr Cys Leu Val Lys Ile Ile Thr Gly Leu Leu Glu Phe Glu Val
                 85                  90                  95

Tyr Leu Glu Tyr Leu Gln Asn Arg Phe Glu Ser Ser Glu Glu Gln Ala
                100                 105                 110

Arg Ala Val Gln Met Arg Thr Lys Asp Leu Ile Gln Phe Leu Gln Lys
                115                 120                 125

Lys Ala Lys Asn Leu Asp Ala Ile Thr Thr Pro Asp Pro Thr Thr Asn
130                 135                 140

Ala Ser Leu Leu Thr Lys Leu Gln Ala Gln Asn Gln Trp Leu Gln Arg
145                 150                 155                 160

Met Thr Thr His Leu Ile Leu Arg Ser Phe Lys Glu Phe Leu Gln Ser
                165                 170                 175

Ser Leu Arg Ala Leu Arg Gln Met
            180

(2) INFORMATION FOR SEQ ID NO:10:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Leu Ala Glu Asn Asn Leu Asn Leu
        50                  55                  60

Pro Lys Met Ala Glu Lys Asp Gly Cys Phe Gln Ser Gly Phe Asn Glu
65                  70                  75                  80

Glu Thr Cys Leu Val Lys Ile Ile Thr Gly Leu Leu Glu Phe Glu Val
            85                  90                  95

Tyr Leu Glu Tyr Leu Gln Asn Arg Phe Glu Ser Ser Glu Glu Gln Ala
            100                 105                 110

Arg Ala Val Gln Met Arg Thr Lys Asp Leu Ile Gln Phe Leu Gln Lys
            115                 120                 125

Lys Ala Lys Asn Leu Asp Ala Ile Thr Thr Pro Asp Pro Thr Thr Asn
        130                 135                 140

Ala Ser Leu Leu Thr Lys Leu Gln Ala Gln Asn Gln Arg Leu Gln Arg
145                 150                 155                 160

Met Thr Thr His Leu Ile Leu Arg Ser Phe Lys Glu Phe Leu Gln Ser
            165                 170                 175

Ser Leu Arg Ala Leu Arg Gln Met
            180

(2) INFORMATION FOR SEQ ID NO:11:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Leu Ala Glu Asn Asn Leu Asn Leu
        50                  55                  60

Pro Lys Met Ala Glu Lys Asp Gly Cys Phe Gln Ser Gly Phe Asn Glu
65                  70                  75                  80

-continued

```
Glu Thr Cys Leu Val Lys Ile Ile Thr Gly Leu Leu Glu Phe Glu Val
             85                  90                  95

Tyr Leu Glu Tyr Leu Gln Asn Arg Phe Glu Ser Ser Glu Glu Gln Ala
            100                 105             110

Arg Ala Val Gln Met Arg Thr Lys Asp Leu Ile Gln Phe Leu Gln Lys
            115             120             125

Lys Ala Lys Asn Leu Asp Ala Ile Thr Thr Pro Asp Pro Thr Thr Asn
        130             135             140

Ala Ser Leu Leu Thr Lys Leu Gln Ala Gln Asn Gln Trp Leu Gln Asp
145                 150             155             160

Met Asp Thr His Leu Ile Leu Arg Ser Phe Lys Glu Phe Leu Gln Ser
                165             170             175

Ser Leu Arg Ala Leu Arg Gln Met
            180
```

(2) INFORMATION FOR SEQ ID NO:12:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Pro Val Pro Pro Gly Glu Asp Ser Lys Asp Val Ala Ala Pro His Arg
1               5                   10                  15

Gln Pro Leu Thr Ser Ser Glu Arg Ile Asp Lys Gln Ile Arg Asp Ile
            20                  25                  30

Leu Asp Phe Ile Ser Ala Leu Arg Lys Glu Thr Cys Asn Lys Ser Asn
            35                  40                  45

Met Cys Glu Ser Ser Lys Glu Ala Asp Ala Phe Trp Asn Leu Asn Leu
        50                  55                  60

Pro Lys Met Ala Glu Lys Asp Gly Cys Phe Tyr Lys Gly Phe Asn Glu
65                  70                  75                  80

Glu Thr Cys Leu Val Lys Ile Ile Thr Gly Leu Leu Glu Phe Glu Val
             85                  90                  95

Tyr Leu Glu Tyr Leu Gln Asn Arg Phe Glu Ser Ser Glu Glu Gln Ala
            100                 105             110

Arg Ala Val Gln Met Arg Thr Lys Asp Leu Ile Gln Phe Leu Gln Lys
            115             120             125

Lys Ala Lys Asn Leu Asp Ala Ile Thr Thr Pro Asp Pro Thr Thr Asn
        130             135             140

Ala Ser Leu Leu Thr Lys Leu Gln Ala Gln Asn Gln Trp Leu Gln Asp
145                 150             155             160

Met Thr Thr His Leu Ile Leu Arg Ser Phe Lys Glu Phe Leu Ile Arg
                165             170             175

Ser Leu Arg Ala Leu Arg Ala Met
            180
```

DNA ENCODING HUMAN IL-6 RECEPTOR ANTAGONIST AND PROTEIN ENCODED THEREBY

CROSS-REFERENCE TO RELATED APPLICATIONS

This is a 371 national stage application of PCT/IT96/00084, filed Apr. 26, 1996, the entire contents of which are herein incorporated by reference.

DESCRIPTION

The present invention relates to antagonists of human interleukin-6 (hIL-6), that are totally incapable of binding the receptor chain (that is to say with gp 130) responsible for transducing the signal associated with this cytokine.

As is known, in known hIL-6 antagonists binding with gp 130 is actually weakened, but not totally abolished. This circumstance may result, in certain cells that are particularly sensitive to the action of the cytokine, in the known hIL-6 antagonists working as weak agonists. For this reason they have no therapeutic use in the formulation of drugs for the treatment of diseases such as multiple myeloma, rheumatoid arthritis, lupus erythematosus and osteoporosis.

There is therefore a need in this specific sector for human interleukin-6 antagonists whose use is not associated with the above risk.

The use of human interleukin-6 antagonists according to the present invention allows all the problems indicated above to be overcome, and also offers other advantages which will become clear from the following.

Subject of the present invention are therefore antagonists of human interleukin-6 (hIL-6), characterised in that they are totally incapable of binding with gp 130 and consist of an amino acid sequence chosen from the group comprising SEQ ID NO:9, SEQ ID NO:10, SEQ ID NO:11 and SEQ ID NO:12.

Another subject of the present invention are: isolated and purified molecules of DNA coding for the interleukin-6 antagonists indicated above; recombinant DNA molecules comprising the DNA molecules mentioned above operatively bound to a sequence controlling expression in said recombinant DNA molecules; a unicellular host transformed using the recombinant DNA molecules, the unicellular host being selected from the group comprising bacteria, yeasts and other fungi, animal cells and plant cells. Further subjects of the present invention are the use of human interleukin-6 antagonists of SEQ ID NO:9, SEQ ID NO:10, SEQ ID NO:11 and SEQ ID NO:12 and of recombinant DNA containing DNA encoding such antagonists for the preparation of pharmaceutical compounds and the use of said antagonists as active principles in the preparation of drugs for the treatment of multiple myeloma, rheumatoid arthritis, lupus erythematosus and osteoporosis.

Up to this point a general description has been given of the present invention. With the aid of the following examples, a more detailed description of a form of embodiment of the invention will now be given, in order to give a clearer understanding of the aims, characteristics, advantages and methods of preparation.

EXAMPLE 1

Figure 1:
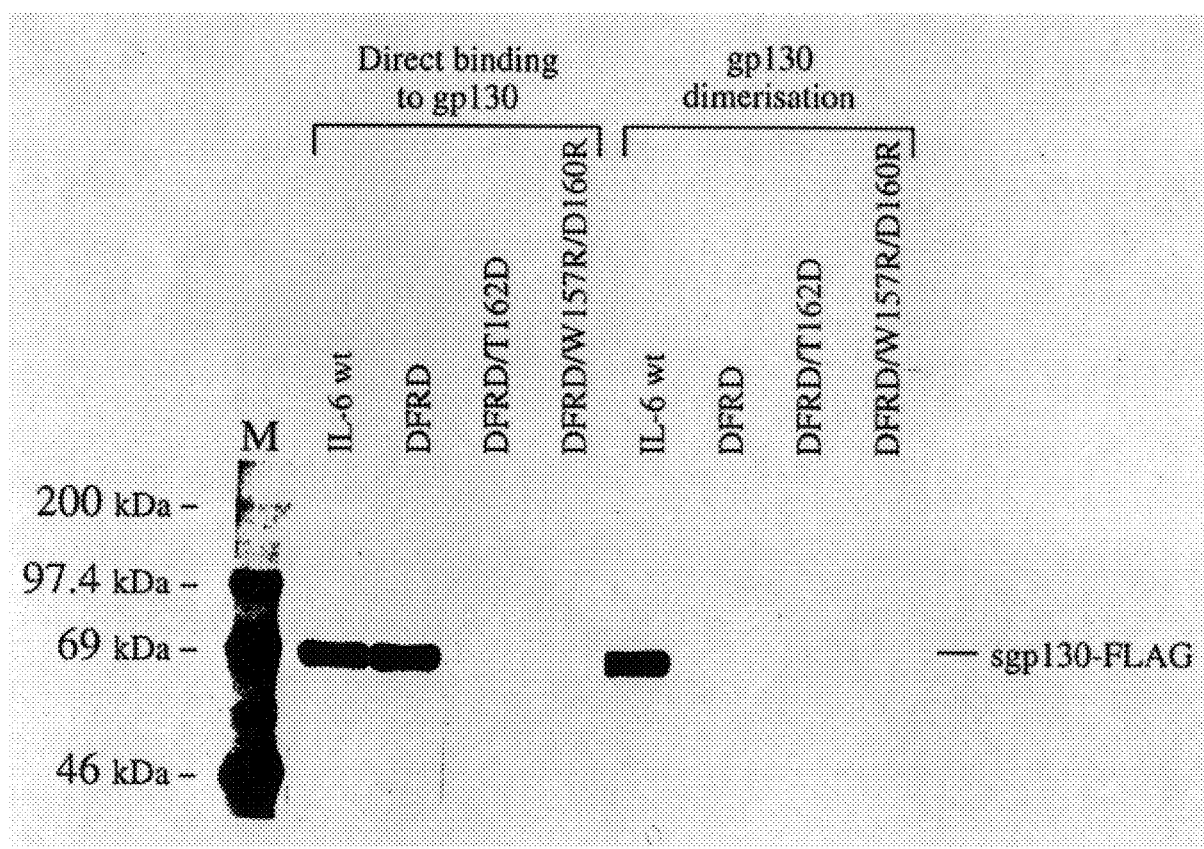
FIG. 1 shows the absence of interaction between antagonists according to the invention and gp 130.

Generation of Interleukin-6 Mutants Using the Method According to the Present Invention In all the mutagenesis reactions the plasmid pT7.7/IL-6/DFRD/Hind was used as a template. This plasmid is a derivative from the plasmid pT7.7 (Studier, F. W. and Moffat, B. A., *J. Mol. Biol.* 189, 113–130, 1986) and contains the coding region of human IL-6 (hIL-6) cloned between sites NdeI and ClaI of the pT7.7 polylinker. The human IL-6 gene is controlled by the T7 RNA polymerase promoter, present in pT7.7. Mutations were introduced into four codons in the region coding for human IL-6 cloned into pT7.7/IL-6/DFRD/Hind (see SEQ ID NO:1), creating the following amino acid substitutions: Tyr31Asp, Gly35Phe, Ser118Arg and Val121Asp. The published international application No. W095/00852 by the same Applicant, claiming Italian priority date 20.06.93, teaches that the introduction of the four amino acid substitutions indicated above into wild-type human IL-6 drastically reduces the biological activity of the cytokine modified in this way, without altering its ability to bind to the hIL-6 receptor itself, thus generating IL-6 DFRD (see SEQ ID NO:8), an effective hIL-6 receptor antagonist. Finally, recognition sites for the following restriction enzymes were introduced without these nucleotide substitutions changing the significance of the respective hIL-6 condons at the moment of translation: SacI in the nucleotidic sequence coding amino acids 20-21-22; BfrI in the nucleotidic sequence coding amino acids 38-39-40; XhoI in the nucleotidic sequence coding amino acids 92-93; HindIII in the nucleotidic sequence coding amino acids 150-151 (see SEQ ID NO:1).

A PCR (Polymerase Chain Reaction) strategy was used to generate mutants within the selected codons in the region coding for human interleukin 6. The downstream primer was IL-6 down Not/Cla, a 45 nucleotide primer, corresponding to positions 530–555 (antisense filament) of the cDNA of hIL-6 (taking the first nucleotide of the first codon of the mature polypeptide to be 1). The primer hybridisation site is in the region of hIL-6 cDNA coding for the carboxy-terminal portion of the protein. The primer IL-6 down Not/Cla also contains a recognition site for the restriction enzyme NotI and a recognition site for the restriction enzyme ClaI, both downstream of the TAG codon, which encodes the end of protein hIL-6 translation.

In the first case, the mutagenetic primer upstream is IL-6 160R/157WR, a primer with 60 nucleotides having the sequence SEQ ID NO:2. The primer IL-6 160R/157WR extends from position 440 to position 499 (sense filament) of the cDNA of hIL-6 and introduces mutations in the codons coding for the amino acid 157 (tryptophan in wild type hIL-6) and 160 (aspartate in wild type hIL-6). A DNA fragment of 135 base pairs is amplified using PCR according to standard PCR amplification methods. Amplification is carried out in 35 cycles. Each cycle consists in incubation for 2 minutes at 94° C. for denaturation of the template, 2 minutes at 50° C. for hybridisation of the oligonucleotide and 3 minutes at 72° C. for extension of the chain. The amplified fragment is digested with HindIII and with ClaI and purified on 2% agarose gel. The fragment generated by PCR and digested by the two enzymes is ligated into the vector pT7.7/IL-6/DFRD/Hind, digested with the same two enzymes, purified on 0.8% agarose gel.

In the second case, the mutagenetic upstream primer is IL-6 T162D, a 64 nucleotide primer whose sequence is SEQ ID NO: 3. The primer IL-6 T162D extends from position 441 to position 503 (sense filament) of the cDNA of hIL-6 and introduces mutations in the codons coding for the amino acid 162 (threonine in wild type hIL-6). A DNA fragment with 134 base pairs is amplified by PCR using standard PCR amplification methods. Amplification is carried out in 35 cycles. Each cycle consists in incubation for 2 minutes at 94° C. for denaturation of the template, 2 minutes at 50° C. for hybridisation of the oligonucleotide and 3 minutes at 72° C. for extension of the chain. The amplified fragment is digested with HindIII and with ClaI and purified on 2% agarose gel. The fragment generated by PCR and digested by the two enzymes is ligated into the vector pT7.7/IL-6/DFRD/Hind, digested with the same two enzymes, purified on 0.8% agarose gel.

The identity of the mutants obtained from both PCR reactions was verified by sequence analysis of single isolates. The amino acid substitutions found in the mutant IL-6 DFRD/D160R are described in SEQ ID NO:9, the amino acid substitutions found in the mutant IL-6 DFRD/W157R/D160R are described in SEQ ID NO:10 and the amino acid substitutions found in the mutant IL-6 DFRD/T162D are described in SEQ ID NO:11.

EXAMPLE 2

Demonstration that binding of the antagonists according to the invention to the specific receptor is unchanged with respect to wild type interleukin-6

The proteins IL-6 DFRD/D160R (coded by the cDNA described in SEQ ID NO:4), IL-6 DFRD/W157R/D160R (coded by the cDNA described in SEQ ID NO:5) and IL-6 DFRD/T162D (coded by the cDNA described in SEQ ID NO:6) were produced according to the state of the art, as described (Arcone, R., Pucci, P., Zappacosta, F., Fontaine, V., Malorni, A., Marino, G., and Ciliberto, G., Eur. J. Biochem. 198, 541–547, 1991). The ability of the mutants to bind to the hIL-6 receptor was measured using state of the art methods, as described (Savino, R., Lahm, A., Salvati, A. L., Ciapponi, L., Sporeno, E., Altamura, S., Paonessa, G., Toniatti, C., Ciliberto, G., EMBO J. 13, 1357–1367, 1994). Table 1 below gives the receptor binding levels for wild type IL-6 and for the mutant forms obtained as described in example 1.

TABLE 1

Ability of the mutants obtained as described in example 1 to bind to the IL-6e receptor

| | |
|---|---|
| Wild type IL-6 | 100% |
| IL-6 DFRD/D160R (SEQ ID NO:9) | 137% |
| IL-6 DFRD/W157R/D160R (SEQ ID NO:10) | 130% |
| IL-6 DFRD/T162D (SEQ ID NO:11) | 39% |

EXAMPLE 3

Demonstration of the Fact that the Antagonists According to the Invention are Totally Incapable of Binding gp 130

The mutants IL-6 DFRD (coded by the cDNA described in SEQ ID NO:1), IL-6 DFRD/W157R/D160R (coded by the cDNA described in SEQ ID NO:5) and IL-6 DFRD/T162D (coded by the cDNA described in SEQ ID NO:6) were tested for their ability to bind gp130. For this purpose the experimental system used is represented by a series of immunoprecipitations in the presence of the two receptor components: the specific IL-6Rα receptor and the transducing sub-unit gp130. These two receptors were produced in insect cells using the expression system known as Baculovirus. Both IL-6Rα and gp130 were expressed as soluble molecules (indicated by the prefix s before the name of the receptor, for example sgp130 or sIL-6Rα), that is to say without the membrane and intra-cytoplasmatic domains. Furthermore, in the case of gp130, several amino acids representing the recognition sites (epitopes) for specific monoclonal antibodies were added before the COOH terminus, immediately before the stop codon. Two types of epitopes were added, known as "myc" (made up of 10 amino acids) and "FLAG" (made up of 8 amino acids), so as to generate two types of molecule: sgp130-myc and sgp130-FLAG.

Likewise, two types of receptor were generated for sIL-6Rα, one without any addition, known as sIL-6Rα, and another with the epitope tag myc, known as sIL-6Rα-myc.

These recombinant receptors were produced in insect cells (denominated High Five) as soluble molecules and then secreted into the cell culture medium. The use of a culture medium containing methionine labelled with radioactive sulphur ($^{35}S$) allowed production of radioactive receptors which were used in the experiments.

The wild type IL-6 and the mutants were produced according to the state of the art, as described (Arcone, R., Pucci, P., Zappacosta, F., Fontaine, V., Malorni, A., Marino, G., and Ciliberto, G., Eur. J. Biochem 198, 541–547, 1991).

The first assay to determine binding of the IL-6 mutants to gp130, known as the gp130 direct binding assay, was carried out as follows. The receptor sIL-6Rα-myc was immobilised on protein A Sepharose beads by means of the anti-myc monoclonal antibody, and incubated with IL-6 or with the above mentioned mutants in the presence of sgp130-FLAG labelled with $^{35}S$. As the latter molecule is not immunoprecipitated by the anti-myc antibody, its immunoprecipitation can only be explained by assuming direct binding to the IL-6/sIL-6Rα-myc complex formed on the beads. After incubation, the beads (with the immobilised complexes) were washed to eliminate excess unbound $^{35}S$-sgp130-FLAG. The beads were then incubated with a solution containing SDS in which the proteins were denatured and the receptor complex formed was dissociated. The whole was then loaded onto SDS-polyacrylamide gel with which it is possible to evaluate the amount of bound $^{35}S$-sgp130-FLAG and therefore the ability of the IL-6 mutants to bind gp130.

As can be seen in the right hand part of FIG. 1 (under the heading "Direct binding to gp130") in this type of assay the mutant IL-6 DFRD is still capable of binding gp130. On the contrary, the mutants DFRD/W157R/D160R and DFRD/T162D are completely incapable of binding gp130.

The second gp130 binding assay has the aim of testing the ability of the mutants to form a receptor complex in which gp130 is present as a dimer. The gp130 dimer is closely related to the ability of the receptor complex to transduce the signal inside the cell. This assay was carried out by immobilising sgp130-myc on Sepharose beads (again using the anti-myc monoclonal antibody) and incubating it with IL-6 (wild type or mutant) in the presence of sIL-6Rα and 35S-sgp130-FLAG. As in the preceding assay, the latter molecule cannot be immunoprecipitated by the anti-myc antibody, and its immunoprecipitation can only be explained by assuming the formation of a receptor complex with the sgp130-myc present on the beads. In this case, after the incubation period and the subsequent washing (to eliminate any excess of 35S-sgp130-FLAG), the presence of 35S-sgp130-FLAG in the receptor complex indicates the formation of a gp130 dimer. As in the preceding case, the beads were then incubated with a solution containing SDS in which the proteins were denatured and the receptor complex formed was dissociated. The whole was then loaded onto SDS-polyacrylamide gel, from which it was possible to evaluate the amount of bound 35S-sgp130-FLAG and therefore the ability of the IL-6 mutants to induce formation of a gp130 dimer. As can be seen in the left hand section of FIG. 1 (under the heading "gp130 Dimerisation"), in this case only wild type IL-6 was capable of inducing the formation of the gp130 dimer. The result confirms that none of the mutants is capable of dimerising gp130 and therefore of forming a receptor complex in which two molecules of gp130 can trigger the signal within the cell.

EXAMPLE 4
Demonstration that the Proteins Modified According to the Present Invention are Functional Antagonists of Human Interleukin 6 in Hepatoma Cells The proteins IL-6 DFRD/W157R/D160R (coded by the cDNA described in SEQ ID NO:5) and IL-6 DFRD/T162D (coded by the cDNA described in SEQ ID NO:6) were selected for analysis of agonistic activity. The biological activity of the two mutants on human hepatoma cells was measured according to the state of the art, as described (Gregory, B., Savino, R. and Ciliberto, G., *J. Immunol. Methods*, 170, 47–56, 1994). Table 2 below indicates the values for biological activity of wild type IL-6 and for the two mutant forms obtained as described in example 1.

TABLE 2

Biological activity of IL-6 and of the mutants obtained as described in example 1

| Wild type IL-6 | 100% |
| IL-6 DFRD/W157R/D160R (SEQ ID NO:5) | 0% |
| IL-6 DFRD/T162D (SEQ ID NO:6) | 0% |

Figure 2:
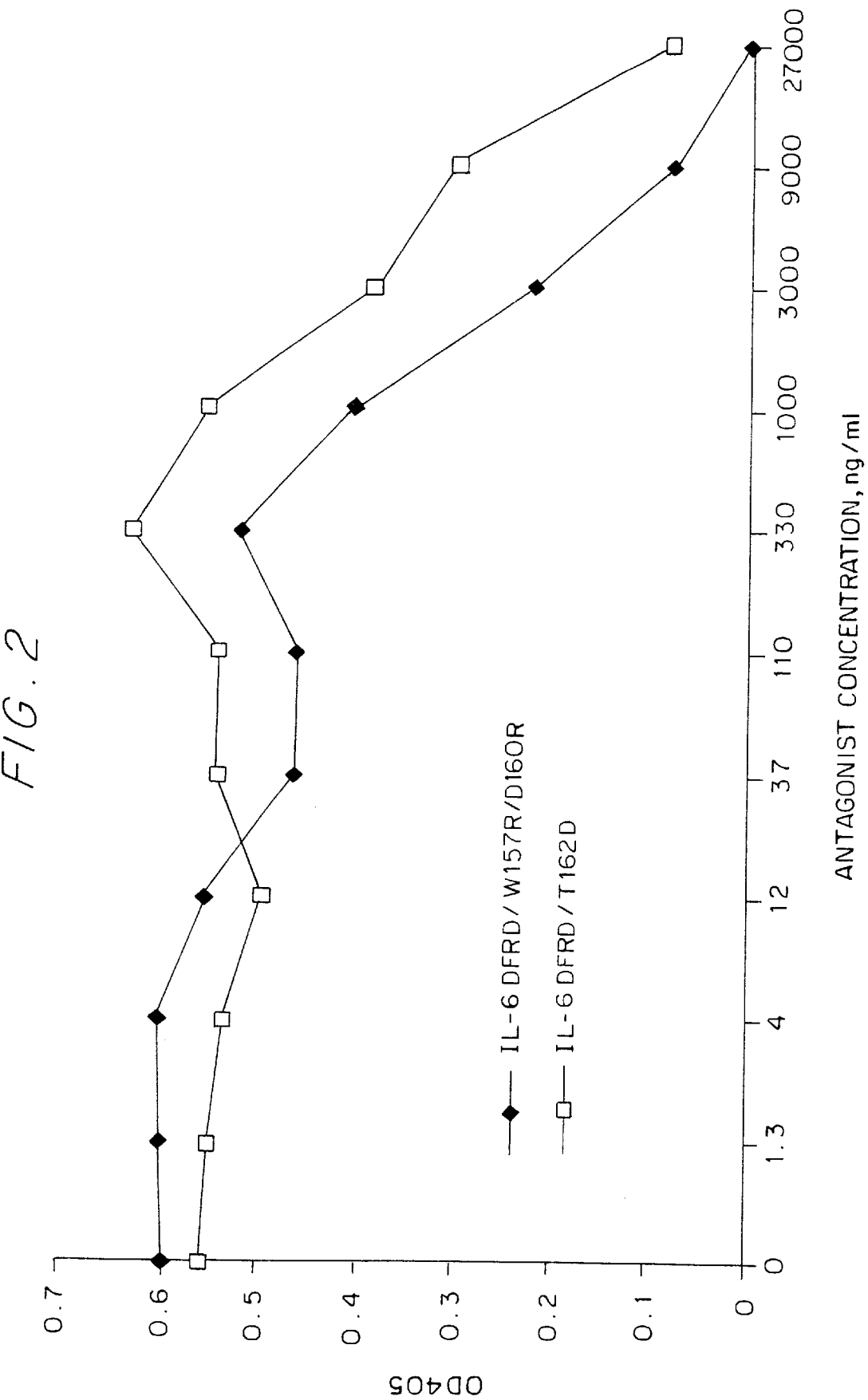
FIG. 2 shows the biological antagonism of the antagonists according to the invention compared to wild type interleukin-6 on human hepatoma cells.

The two variants IL-6 DFRD/W157R/D160R (SEQ ID NO:10) and IL-6 DFRD/T162D (SEQ ID NO:11) show no sign of biological activity in human hepatoma cells, they still have the ability to bind the receptor gp80, but have completely lost the ability to bind gp130, as described in example 3. They were therefore used in competition tests on the biological activity of wild type interleukin 6 in human hepatoma cells. The cells were stimulated with wild type interleukin 6 at 4 nanogrammes per millilitre (ng/ml) of culture medium, in the presence of increasing concentrations of the two mutants. As illustrated in FIG. 2 (in which the biological activity of wild type interleukin 6 is expressed in arbitrary units), increasing concentrations of the mutant are capable or efficiently antagonising the effects of wild type interleukin 6 on the human hepatoma cells.

EXAMPLE 5
Generation of a Further Interleukin-6 Mutant Using the Method According to the Present Invention, Demonstration of the Fact that it is Totally Incapable of Binding gp130 and that is a Functional Antagonist of Human Interleukin-6

As already mentioned in Example 1, publication WO95/00852 by the same Applicant, claiming Italian priority date 20.06.93, teaches that the introduction of the four amino acid substitutions Tyr31Asp, Gly35Phe, Ser118Arg and Val121Asp into wild-type human IL-6 drastically reduces the biological activity of the cytokine modified in this way, without altering its ability to bind to the hIL-6 receptor itself, thus generating IL-6 DFRD (see SEQ ID NO:8), an effective hIL-6 receptor antagonist. Moreover, example 3 above has shown that IL-6 DFRD, although unable to dimerize gp130, is still capable of binding gp130 itself. The international patent application PCT/IT95/00216 filed by the same Applicant 13.12.95, claiming Italian priority 14.12.94, describes that the introduction of the five amino acid substitutions Gln75Tyr, Ser76Lys, Gln175Ile, Ser176Arg and Gln183Ala into IL-6 DFRD strongly increases its ability to bind to the hIL-6 receptor and decreases the amount of protein necessary to inhibit wild-type hIL-6 activity on both human hepatoma and on human myeloma cells, thus generating Sant5, a much more potent hIL-6 receptor antagonists.

Using the Polymerase Chain Reaction (PCR) molecular biology technique, the three amino acid substitutions Leu57Asp, Glu59Phe and Asn60Trp were inserted into Sant5 thus generating mutant protein Sant7, whose amino acid substitutions are described in SEQ ID NO:12.

The mutant protein Sant7 was produced according to the state of the art, as described (Arcone, R., Pucci, P., Zappacosta, F., Fontaine, V., Malorni, A., Marino, G., Ciliberto, G., *Eur. J. Biochem.* 198, 541–547, 1991). The ability of Sant7 to bind to the hIL-6 receptor was measured using the state of the art methods, as described (Savino,-R., Lahm, A., Salvati, A. L., Ciapponi, L., Sporeno, E., Altamura, S., Paonessa, G., Toniatti, C., Ciliberto, G., *EMBO J.* 13, 1357–1367, 1994). Table 3 below gives the receptor binding capacity for wild type IL-6 and for Sant7.

TABLE 3

Ability of Sant7 to bind the IL-6 receptor (% of the wild-type IL-6)

| Wild type IL-6 | 100% |
| Sant7 | 6500% |

As can be seen from the table, also Sant7, like the parental mutant Sant5 (as described in PCT patent application number IT9500216 filed by the same Applicant 13.12.95), has a binding capacity for the specific IL-6 receptor increased with respect to wild-type IL-6.

Figure 3:
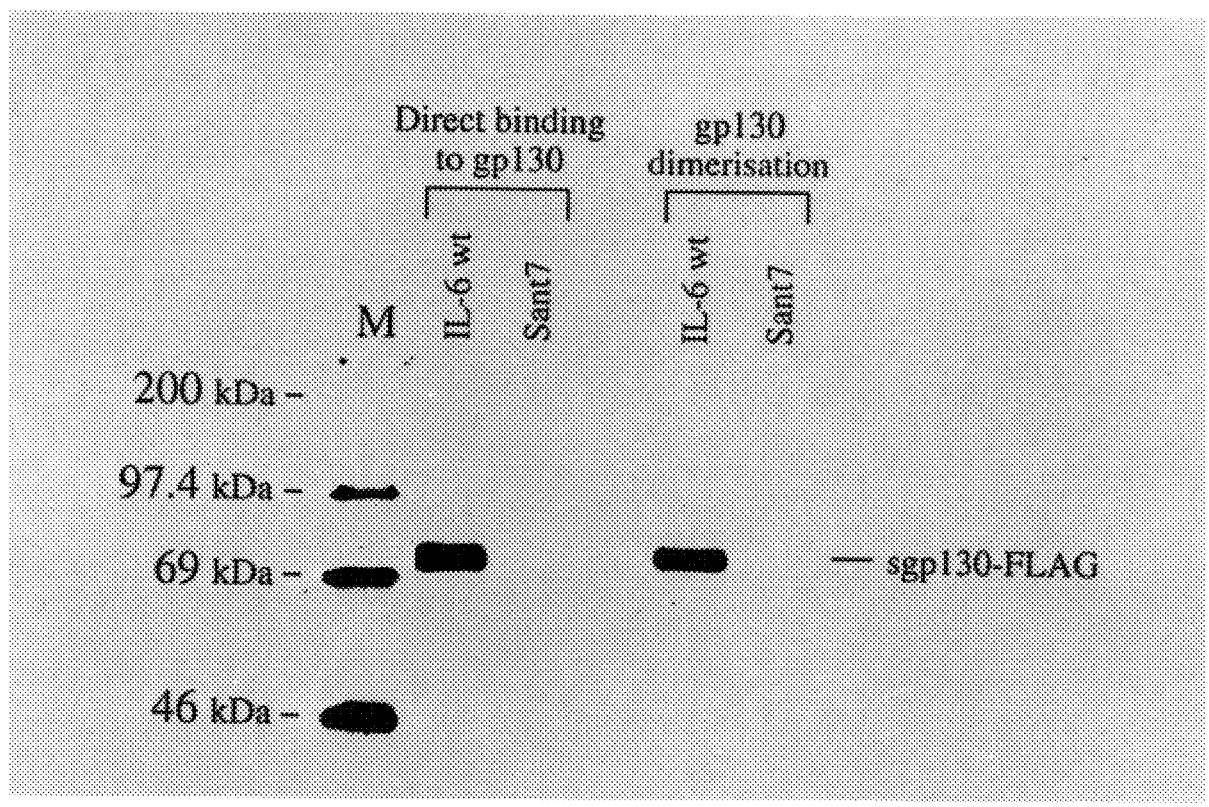
FIG. 3 shows the absence of gp130 interaction of the mutant Sant 7 according to the present invention.

The ability of Sant7 in binding to gp130 was tested with the same techniques described in the example 3. As can be seen in the right hand part of FIG. 3 (under the heading "Direct binding to gp130) in this type of assay the mutant Sant7 is completely uncapable of binding gp130 (unlike the parental mutant DFRD). The ability of Sant7 to form a receptor complex in wich gp130 is present as a dimer was also tested with the same tecnique described in the example 3. As can be seen in the left hand part of FIG. 3 (under the heading "gp130 Dimerisation"), only wild-type IL-6 is capable of inducing the formation of the gp130 diner, therefore Sant7 is not able to form a receptor complex in which two molecules of gp130 can trigger the signal inside the cell.

The ability of Sant7 to inhibit wild-type hIL-6 biological activity was tested on Hep3B human hepatoma cells, according to the state of the art, as described (Savino, R., Lahm, A., Salvati, A. L., Ciapponi, L., Sporeno, E., Altamura, S., Paonessa, G., Toniatti, C., Ciliberto, G., *EMBO J.* 13, 1357–1367, 1994). We also tested the ability of Sant7 to fully inhibit the interleukin 6-dependent growth of two human myeloma cell line, called XG-1 and XG-2, derived from freshly isolated myeloma cells from patients with terminal disease. The XG-1 and XG-2 myeloma cell lines growth is dependent on exogenously added interleukin 6, similarly to what has been shown for fresh myeloma cells, therefore these cell lines can be considered an excellent in vitro model of the multiple myeloma disease (Jourdan, M., Zhang, X-G., Portier, M., Boiron, J.-M., Bataille, R. and Klein, B.(1991) *J. Immunol.* 147, 4402–4407). Table 4 show the concentrations of Sant7 (expressed in nanograms of mutant per milliliter of colture medium) necessary to inhibit 90% of interleukin 6 biological activity (hepatoma cells were stimulated with 4 nanograms of wild type interleukin 6 per milliliter of colture medium, while XG-1 myeloma cells were stimulated with 0.1 nanograms and XG-2 with 0.5 nanograms of interleukin 6 per milliliter of colture medium, due to the higher sensitivity of the latter cells to wild type interleukin 6).

TABLE 4

Inhibition of wild-type interleukin-6 biological activity by Sant7 on both hepatoma and myeloma cells.

| hIL-6 Mutant | 90% inhibition of interleukin-6 activity on | | |
|---|---|---|---|
| | hepatoma cells | myeloma cells | |
| | Hep3B | XG-1 | XG-2 |
| Sant7 | 30 ng/ml | 35 ng/ml | 950 ng/ml |

As can be seen from the table, Sant7 behaves as a very effective interleukin-6 receptor antagonist on all cell lines tested.

We claim:

1. A human interleukin-6 (hIL-6) receptor antagonist which is incapable of binding gp 130 and which comprises an amino acid sequence selected from the group consisting of SEQ ID NO:9, SEQ ID NO:10, SEQ ID NO:11 and SEQ ID NO:12.

2. A composition, comprising a pharmaceutically-acceptable carrier, excipient or auxiliary and a human interleukin-6 receptor antagonist according to claim 1.

3. The human interleukin-6 receptor antagonist according to claim 1 which comprises the amino acid sequence of SEQ ID NO:9.

4. The human interleukin-6 receptor antagonist according to claim 1 which comprises the amino acid sequence of SEQ ID NO:10.

5. The human interleukin-6 receptor antagonist according to claim 1 which comprises the amino acid sequence of SEQ ID NO:11.

6. The human interleukin-6 receptor antagonist according to claim 1 which comprises the amino acid sequence of SEQ ID NO:12.

7. A DNA molecule encoding a human interleukin-6 receptor antagonist which is incapable of binding gp130 and which comprises an amino acid sequence selected from the group consisting of SEQ ID NO:9, SEQ ID NO:10, SEQ ID NO:11, and SEQ ID NO:12.

8. The DNA molecule according to claim 7, which is an isolated DNA molecule.

9. The isolated DNA molecule according to claim 8, wherein said isolated DNA molecule comprises a nucleotide sequence selected from the group consisting of SEQ ID NO:4, SEQ ID NO:5, SEQ ID NO:6 and SEQ ID NO:7.

10. A composition, comprising a pharmaceutically-acceptable carrier, excipient or auxiliary and an isolated DNA molecule according to claim 9.

11. A recombinant DNA molecule comprising the DNA molecule according to claim 9 operatively linked to a sequence controlling the expression of said interleukin-6 antagonist in said molecule.

12. A host cell transformed with the recombinant DNA molecule according to claim 11.

13. The host cell according to claim 12, wherein said host cell is selected from the group consisting of bacteria, yeasts, fungi, animal cells and plant cells.

14. The isolated DNA molecule according to claim 9, wherein said isolated DNA molecule comprises the nucleotide sequence of SEQ ID NO:4.

15. The isolated DNA molecule according to claim 9, wherein said isolated DNA molecule comprises the nucleotide sequence of SEQ ID NO:5.

16. The isolated DNA molecule according to claim 9, wherein said isolated DNA molecule comprises the nucleotide sequence of SEQ ID NO:6.

17. The isolated DNA molecule according to claim 9, wherein said isolated DNA molecule comprises the nucleotide sequence of SEQ ID NO:7.

* * * * *